United States Patent [19]

Sutherland et al.

[11] Patent Number: 5,401,255
[45] Date of Patent: Mar. 28, 1995

[54] MULTI-FUNCTIONAL VALVE WITH UNITARY VALVING MEMBER AND IMPROVED SAFETY

[75] Inventors: Karl Sutherland, Laguna Hills; Frederick J. Reinhart, Newport Beach; Terry Sprague, Chino Hills, all of Calif.

[73] Assignee: Baxter International Inc., Deerfield, Ill.

[21] Appl. No.: 94,834

[22] Filed: Jul. 20, 1993

[51] Int. Cl.⁶ ............................................ A61M 16/00
[52] U.S. Cl. .................................................... 604/247
[58] Field of Search ................. 604/4, 118, 151, 247, 604/319, 9, 246, 248, 249; 137/853, 512.3

[56] References Cited

U.S. PATENT DOCUMENTS

| | | |
|---|---|---|
| 2,897,835 | 8/1959 | Philippe . |
| 3,417,775 | 12/1968 | Smith ................................ 137/853 |
| 3,675,891 | 7/1972 | Reynolds et al. .................... 604/118 |
| 3,967,645 | 7/1976 | Gregory ............................. 604/247 |
| 4,303,072 | 12/1981 | Lewis . |
| 4,502,502 | 3/1985 | Krug . |
| 4,532,081 | 4/1986 | Fillman . |
| 4,568,333 | 2/1986 | Sawyer et al. . |
| 4,610,275 | 9/1986 | Beecher . |
| 4,642,097 | 2/1987 | Siposs . |
| 4,671,786 | 6/1987 | Krug . |
| 4,725,266 | 2/1988 | Siposs . |
| 4,758,224 | 7/1988 | Siposs . |
| 4,919,167 | 4/1990 | Mansker ............................. 137/853 |
| 4,944,732 | 7/1990 | Russo ................................ 604/247 |
| 5,137,522 | 8/1992 | Bron . |

FOREIGN PATENT DOCUMENTS

| | | |
|---|---|---|
| 497576 | 1/1992 | European Pat. Off. . |
| 473261 | 3/1992 | European Pat. Off. . |
| 2672802 | 2/1992 | France . |
| 4107044 | 3/1991 | Germany . |
| 4207917 | 3/1992 | Germany . |
| WO90/11465 | 10/1990 | WIPO . |

*Primary Examiner*—John D. Yasko
*Assistant Examiner*—Manuel Mendez
*Attorney, Agent, or Firm*—Poms Smith Lande & Rose

[57] ABSTRACT

A pressure-responsive control valve is especially useful to control aspiration of fluids from a patient during a surgical procedure. The control valve includes features which control the aspiration suction level communicated to the patient, which prevent reverse flow positive pressure from communicating to the patient, which safely vents such a reverse flow positive pressure in the event it reaches a level jeopardizing the integrity of the valve or plumbing fixtures, and which prevents aspirated fluids from weeping from the valve into the surgical environment in the event that a positive pressure communicates to the inlet of the control valve.

23 Claims, 3 Drawing Sheets

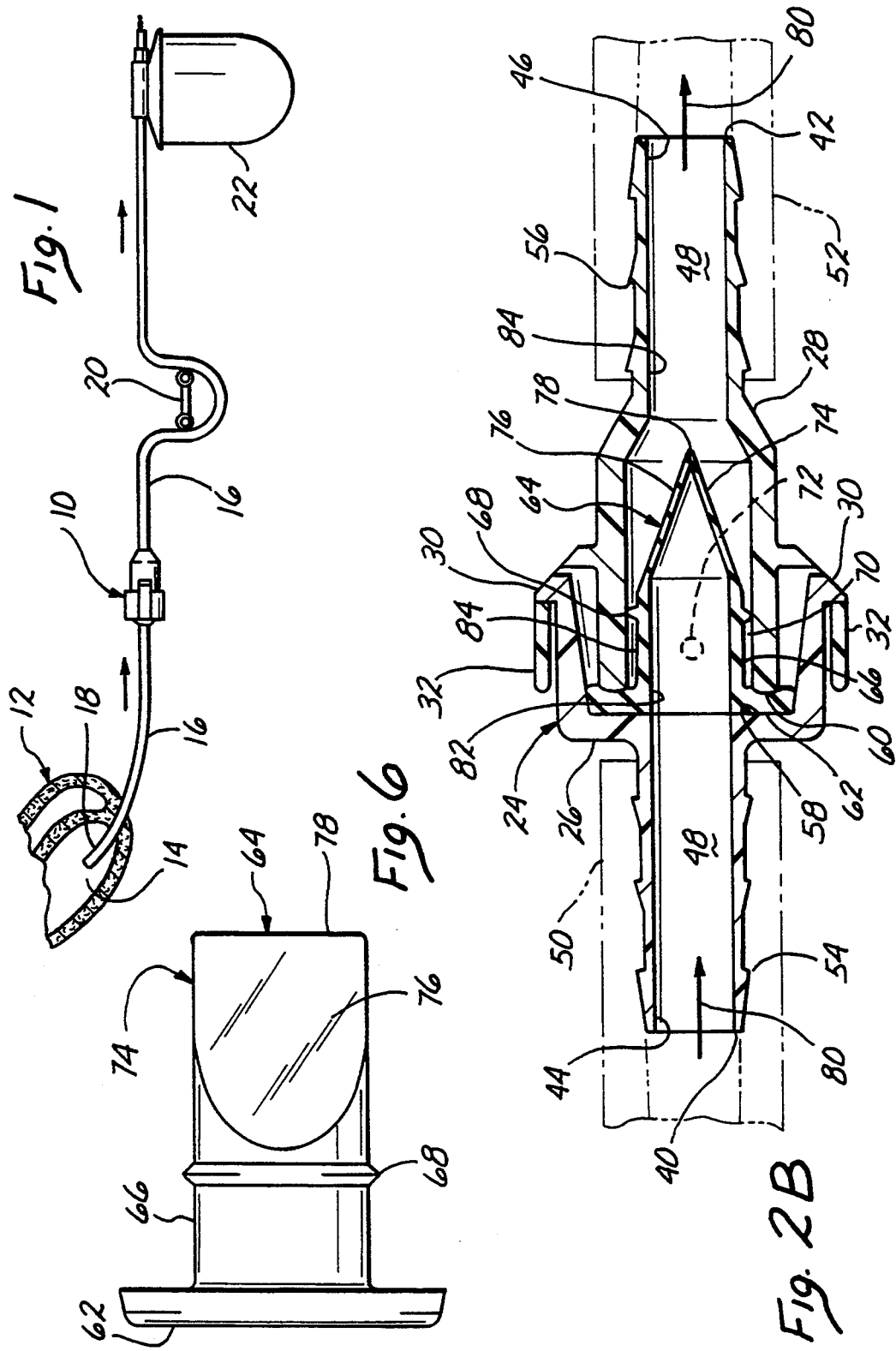

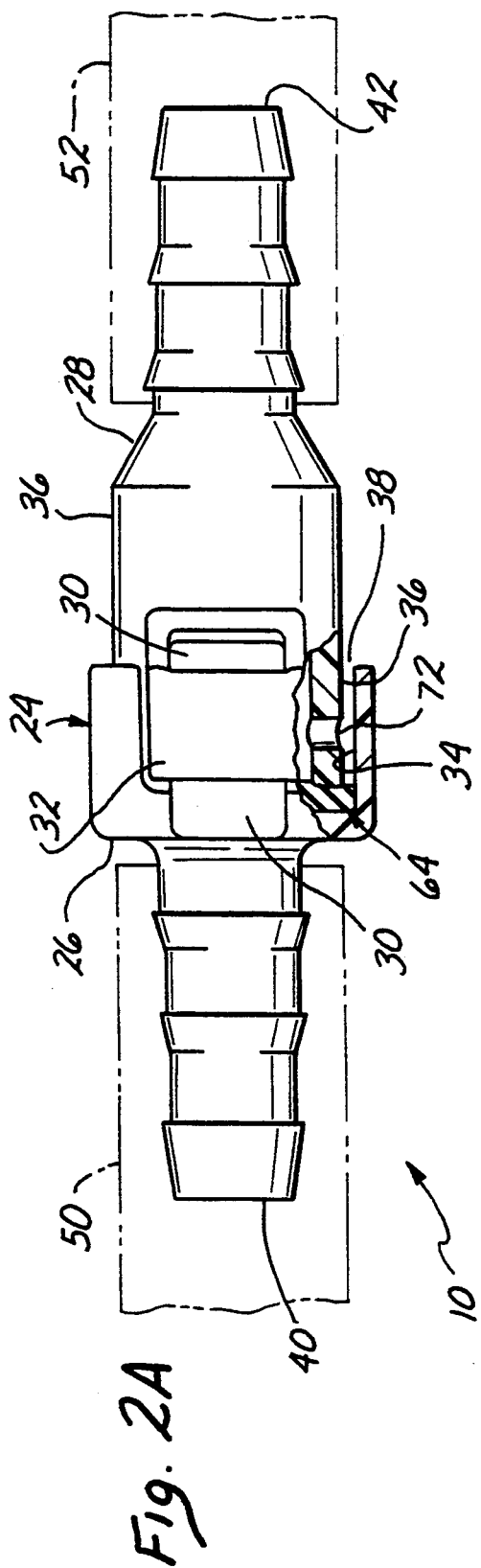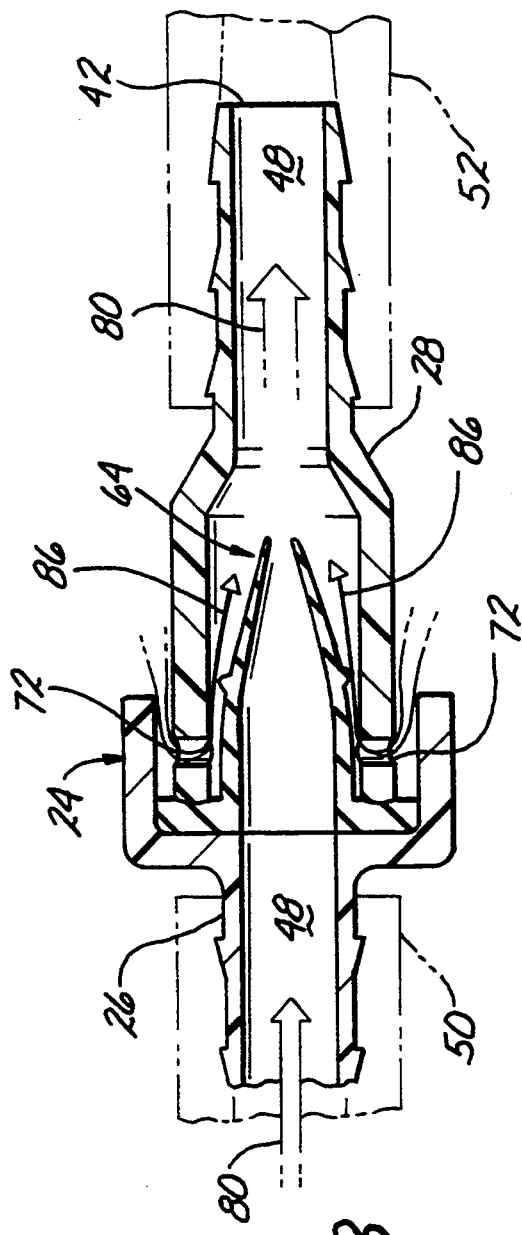

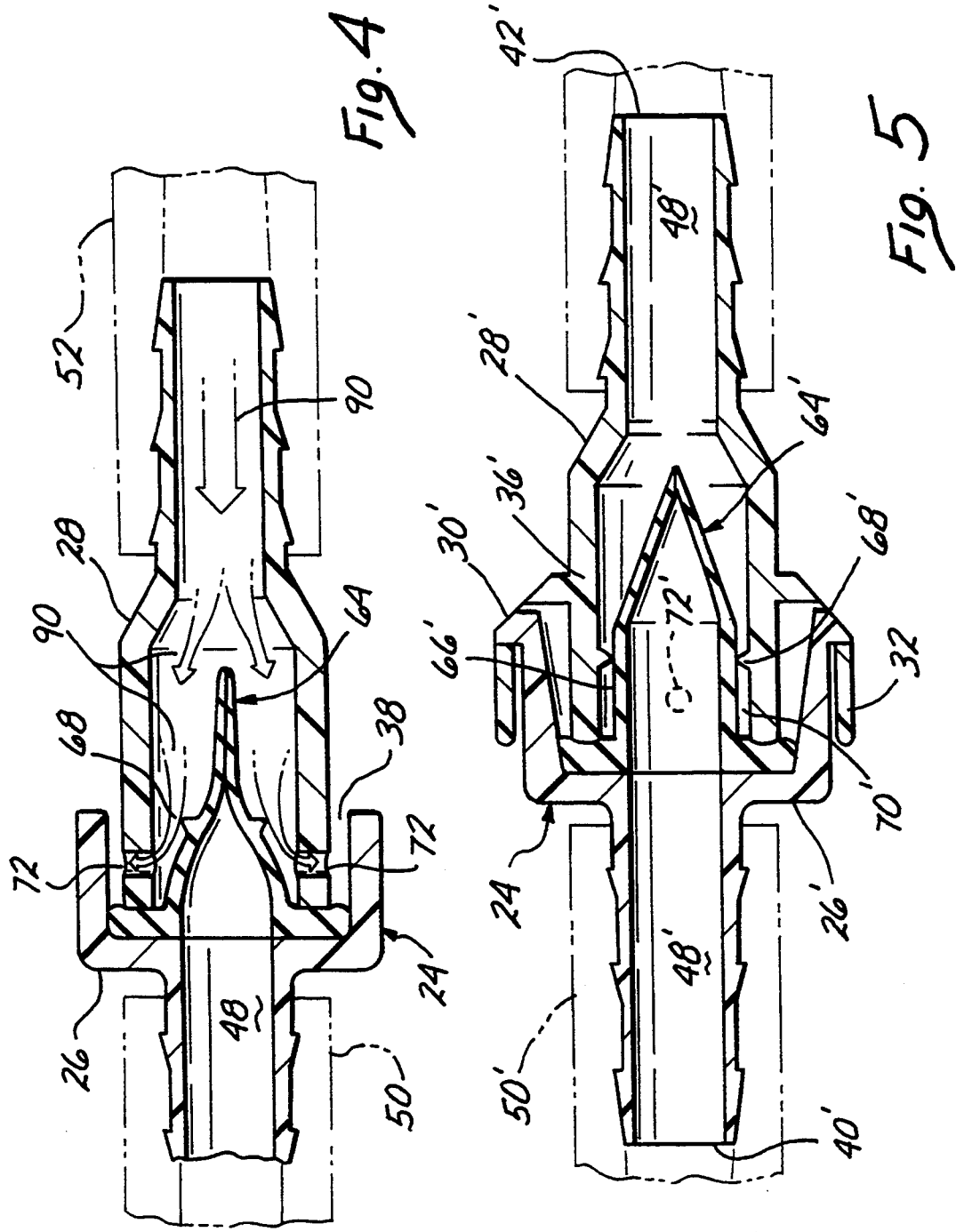

MULTI-FUNCTIONAL VALVE WITH UNITARY VALVING MEMBER AND IMPROVED SAFETY

BACKGROUND OF THE INVENTION

1. Field of the Invention

The present invention is in the field of multi-function valves. More particularly, the present invention relates to a multi-function valve having particular utility in the performance of open-heart surgery. Still more particularly, the present invention relates to a multi-function valve useful during open heart surgery for controlling aspirated fluid flow from the left ventricle of the heart to an aspiration pump by controlling the level of aspiration suction applied at the heart, for preventing inadvertent reverse flow of fluid to the heart, for safely and controllably venting reverse flow positive pressure which would cause such reverse flow of fluid to the heart, and for controlling inlet positive pressure at the control valve, which inlet positive pressure causes conventional control valves to undesirably weep patient's blood into the operating room environment.

2. Related Technology

In the performance of open heart surgery, generally the heart is bypassed and the patient's blood circulation is maintained by use of a heart-lung machine. However, a certain amount of blood finds its way into the left ventricle of the heart. Unless this blood is removed, the left ventricle of the heart is distended and resuscitation of the heart at the conclusion of the procedure is made more difficult or impossible.

Accordingly, some physicians insert a drain tube into the left ventricle and use a positive-displacement aspiration pump to remove the accumulated blood. The speed of operation of such a pump positive-displacement aspiration pump determines the rate at which the pump will aspirate blood from the left ventricle. An insufficient rate of aspiration can still allow blood to accumulate in the left ventricle. On the other hand, an excessive aspiration rate may cause the drain tube to suck against the heart tissues, thereby causing trauma. One former but currently unpopular solution to this problem is to have the speed of the positive-displacement aspiration pump controlled by a technician. However, this solution requires additional operating room personnel and requires additional communication from the physician to the technician.

Another conventional and currently common solution is to use a positive-displacement aspiration pump, for example, a pump of the roller type, and to control its operational speed to a constant level throughout the surgical procedure. In order to control the level of aspirating suction applied to the left ventricle of the heart during the surgical procedure, a pre-set negative pressure relief valve is generally disposed in the suction line between the heart and the positive-displacement aspiration pump. This valve controls the suction applied to the heart by venting ambient air into the suction line downstream of the valve.

Such a suction control valve may also include a check valve safety feature which prevents reverse flow of fluid toward the heart in the event that plumbing is connected incorrectly during the procedure, or should the aspiration pump be operated in reverse, or should the aspiration pump be stopped with a pressurized reservoir downstream of the pump, for example, causing a positive pressure reverse flow toward the heart.

However, such a reverse flow positive pressure check valve function results in the blood aspiration plumbing, which has been designed to withstand suction, being exposed to an unregulated positive pressure. If the reverse flow positive pressure is high enough, the result can occasionally be the blowing off of an aspiration tube from a hose barb with resultant spray of blood into the operating room. In the event that the aspiration plumbing does not blow apart and the reverse flow positive pressure is high enough, the check valve may be overcome so that a catastrophic reverse positive pressure flows to the patient's heart.

Consequently, the control valve may also include a positive pressure venting feature which relieves such a reverse flow positive pressure. This feature insures that aspiration plumbing is not blown apart by such a reverse positive pressure. Also, this venting feature insures that the valve itself is not overcome by a sufficiently high reverse positive pressure such that fluid forces its way past the valve and to the heart.

Of course, operation of this safety feature of the control valve results in undesirable release of patient's blood into the operating room environment. That is, it is recognized that if the positive pressure were not controlled by venting at the control valve or elsewhere, it could possibly result in an uncontrolled venting of the pressure or a catastrophic reverse flow to the patient's heart. As explained above, aspiration tubing could be blown off of a hose barb fitting at a pressure higher than the venting pressure, and with resultant blood spray into the operating room totally without control of the direction or location of the resulting spray. Alternatively the check valve could be overcome so that fluid flows in reverse to the patient's heart. The former type of uncontrolled relief of an inadvertent positive pressure would be hazardous to operating room personnel. The latter type of reverse flow to the patient's heart could be fatal.

As a result, the controlled venting of blood at the control valve when necessary to vent such an unintended reverse positive pressure is an acceptable operational aspect of the conventional control valves. However, on the rare occasions when this positive pressure relief safety feature does function it is the result of an infrequent personnel or equipment error which could be catastrophic for the patient. Further, it is recognized that the venting of patient blood into the operating room environment because of a very infrequent reverse flow positive pressure of such magnitude is an accepted and necessary safety function. Preferably, the operating room personnel will have arrange the plumbing and the location of the control valve to minimize the risk from this venting function, should it occur. That is, the blood vented from the control valve is generally arranged at a controlled location near the floor of the operating room, and the venting is preferably is at a relatively low velocity so that spray and misting of blood into the operating room air is avoided.

Along the above line, U.S. Pat. No. 4,642,097, issued Feb. 10, 1987, to G. Siposs, is believed to teach a control valve in which ambient air flow to a negative pressure vent port is controlled by a cammed sleeve member which is axially movable along a body of the control valve. A duck bill check valve member prevents reverse flow from the aspiration pump to the heart. Also, a sleeve-type positive pressure relief valve vents the passage downstream of the check valve member to ambient to prevent excessive pressure build up on that side of the control valve.

With a control valve as taught by the Siposs '097 patent, a physician or another person must adjust the control valve to set the venting level necessary to maintain a desired suction at the heart in view of the operating speed and pumping characterists of the aspiration pump. This set venting level continuously admits atmospheric air to the passage leading to the aspiration pump and results in an undesirably large amount of air being mixed with the aspirated blood. Also, the venting function is set and does not self-adjust in the event the speed of the aspiration pump, or other such factor which affects the level of suction at the heart, changes during the surgical procedure. Notably, this control valve uses a sleeve-type of positive pressure relief valve which does properly and controllably vent reverse flow positive pressure should such a pressure be applied to the valve. However, the direction of discharge and velocity of the vented blood are not predictable or controlled.

However, with conventional control valves in the event that the aspiration pump is stopped with the conduit between the heart and the control valve filled with fluid another deficiency comes to light. That is, the static fluid column pressure applies between the heart and the control valve applies a positive pressure at the inlet of the control valve, and can be enough to cause dripping and spitting of blood past the sleeve-type vent valve into the operating room environment. Such inlet positive pressure blood weeping from conventional control valves is much more common than blood venting because of inadvertent reverse positive pressure to the control valve. Because this unintended venting of blood from inlet positive pressure to the control valve is so common, it is especially undesirable in the present medical environment. That is, the present medical environment includes risk factors for exposure to AIDS and Hepatitis through blood contact. As is well known, the present medical environment emphasizes all possible controls over exposure of operating room and other medical personnel to patient's blood.

A later U.S. Pat. No. 4,758,224, issued Jul. 19, 1988, also to G. Siposs, is believed to teach a similar control valve which also uses a duck bill check valve member, and a sleeve valve positive pressure relief valve. However, the control valve taught by this patent uses an umbrella-type of negative pressure relief valve so that the physician does not need to adjust the valve to control the maximum suction level applied to the patient's heart. This umbrella type valve is disposed in a chamber situated laterally of and communicating with the main fluid flow path through the valve.

With a control valve as set forth in the Siposs '224 patent, the disadvantage outlined above with respect to undesirable loss of blood into the operating room environment still exists. That is, the sleeve valve type of positive pressure relief valve can still be forced open simply by the liquid column pressure of the blood in the aspiration conduit if the aspiration pump is stopped with this conduit full of liquid. The necessary safety factor of a positive pressure relief function with this valve also presents the undesirable possibility that patient's blood may be released into the operating room environment from the control valve.

Yet another conventional control valve is set out in U.S. Pat. No. 4,725,266, issued Feb. 16, 1988, also to G. Siposs. The Siposs '266 patent is believed to teach a control valve in which a duck bill valve member serves as both a check valve allowing fluid flow only toward the aspirating pump, and also includes a circumferentially and axially extending resilient cylindrical body portion which sealingly cooperates with the valve body at a negative pressure relief port. When the negative pressure in the conduit leading to the aspiration pump reaches a predetermined maximum, the cylindrical portion of the duck bill valve member yields to allow introduction of ambient air and limits the maximum suction applied to the patient's heart.

However, the control valve according to the '266 patent still uses the familiar sleeve type valve for positive pressure relief so that the disadvantage of unintended release of patient's blood into the operating room from the control valve because of an inlet positive pressure is still present.

Still another control valve is seen in two related U.S. Pat. Nos., 4,502,502; and 4,671,786, issued Mar. 5, 1985, and Jun. 9, 1987, respectively, to J. Krug. These control valves use the familiar duck bill valve member to perform the check valve function. Also, the negative pressure relief valving function is performed by an umbrella valve member disposed in a lateral chamber like that seen in the '224 patent to Siposs. However, the positive pressure relief valving function is performed by a second umbrella valve controlling communication outwardly from this lateral chamber to ambient.

The control valves taught by the Krug '502, and '786 patents also suffer from the undesirable weeping or dribbling of patient's blood into the operating room environment because of an inlet positive pressure created by a fluid column pressure in the aspiration tubing, as was discussed earlier. That is, the choice of an umbrella type of positive pressure relief valve does not eliminate this problem of all of the conventional control valves discussed herein.

The conventional control valves all accept the necessary controlled venting of blood which could result in the unlikely event of incorrect plumbing connection, reverse operation of the aspiration pump, or stopping of the pump with a pressurized reservoir downstream of the pump causing pressurized blood backflow. However, these occurrences are rare, and the safety function of the valve is necessary to prevent catastrophic injury to the patient.

On the other hand, the spitting of blood into the operating room environment from the positive pressure vent valve simply because of fluid column pressures in the connecting tubing is a common occurrence, and is objectionable because of its frequency. This blood on the operating room floor at the very least presents an undesirable mess and cleaning burden in the operating room, as well as a risk that personnel will slip and fall on the blood. Moreover, the risk of AIDS or Hepatitis exposure because of contact with patient's blood can not be ignored. A positive pressure vent valve should not allow this unintended release of patient's blood caused by a positive fluid pressure communicating to the inlet of the valve.

Also, the existence of a lateral chamber on the valves of Krug (and on the '224 valve of Siposs) which requires a laterally projecting boss within which to define this lateral chamber, undesirably presents a projection on the exterior of the control valve. Of course, this projection is a hindrance to handling of the control valve and its attached tubing in the operating room environment because this attached tubing and other nearby tubing as well as wiring and instrument cables, for example, may catch on the projection form the control valve. All of the discussed control valves also suffer from an undesirable complexity in their construction, with an excessive parts count.

Finally, the conventional control valves seem by their designs to accept the inevitability of unpredictable venting of patient's blood if a reverse flow positive pressure level applied to the valve reaches the venting pressure level. That is, this safety venting feature is accepted as necessary, but the consequences of this feature operating are not dealt with in the designs of conventional control valves. A control valve should allow this venting only in a fashion best preserving safety for surrounding operating room personnel.

SUMMARY OF THE INVENTION

In view of the deficiencies of conventional control valves, it is a primary object for this invention to provide a multi-function control valve which eliminates the undesirable release of patient's blood into the operating room environment as a result of liquid column pressure applied to the valve.

Also it is an object for the present invention to provide a multi-function control valve which is less complex in structure than the conventional control valves.

Still further, an object for this invention is to provide a multi-function control valve which avoids projections on the housing of the valve which could catch on environmental tubing, wiring, and cables in the operating room.

Accordingly, the present invention provides a multi-function control valve having an elongate housing defining an inlet at one end thereof, an outlet at an opposite end thereof, and a flow path extending between the inlet and outlet to communicate a flow of aspirated patient blood therebetween, a multi-function valve member sealingly disposed in the flow path and including a check valve feature preventing fluid flow from the outlet to the inlet, a vent port opening outwardly from the flow path downstream of the check valve feature, the multi-function valve member including a pressure-responsive yieldable feature sealingly cooperating with the housing to prevent fluid flow through the vent passage and defining a pressure responsive area communicating with the inlet port but isolated from the outlet port by the check valve feature, the yieldable feature on the one hand yielding in response to a certain level of negative pressure in said flow path to admit ambient air thereto, and on the other hand the yieldable feature yielding in response to a determined level of pressurized fluid communicating to the outlet port to vent pressurized fluid from said vent port, whereby pressurized fluid communicating with the inlet port communicated with the outlet port via the check valve feature but also acts on the pressure-responsive area of the yieldable feature to maintain the latter in sealing relation with said housing so that pressurized fluid is not vented from the vent port.

According to a preferred exemplary embodiment of the invention, the valve member takes the form of a duck bill check valve member with a slightly elongated cylindrical portion which inwardly defines a pressure-responsive area communicating with the inlet port but isolated from the outlet port by the check valve lips of the duck bill valve. The duck bill valve member outwardly sealingly cooperates with the housing at the vent port to control fluid flow through this vent port. Outwardly, the duck bill member also defines a pressure responsive area communicating with the vent port. Consequently, when the negative pressure (suction) within the flow path reaches a determined level, the cylindrical portion of the duck bill valve member unseals from the housing to allow entry of ambient air. When a positive pressure at or above a certain level communicates with the outlet port of the valve, the duck bill member partially collapses to unseal from the housing and allow this positive pressure to safely vent to ambient. However, in the event that pressurized fluid communicates to the inlet port of the valve, as may happen when a column of fluid is in the tubing leading from a patient's chest to the inlet of the valve, this positive pressure is communicated to the outlet port past the duck bill check valve lips of the valve. However, this positive pressure also acts on the pressure-responsive interior surface of the cylindrical portion of the duck bill valve member. This internal pressure prevents the duck bill valve member from collapsing at its cylindrical portion and prevents patient's blood from being vented from the control valve.

An additional advantage of the present invention resides in the multi-functional aspect of its few component parts. That is, the entire functional repertoire of the control valve, including a check valve function, a positive pressure relief function, a negative pressure relief function, and a positive pressure containment function when the positive pressure is communicated to the inlet of the control valve, is achieved with a structure preferably having a total of three parts. That is, the housing of the valve may preferably be made of two sealingly cooperating parts, which define the inlet, outlet, and vent ports, and which sealingly capture the slightly elongated duck bill valve member therebetween.

Importantly, in addition to achieving a function not provided by the conventional control valves (inlet positive pressure containment), the present control valve has a sleek housing outer configuration without external projections which could catch surrounding tubing, wires or other operating room fixtures. Accordingly, the present invention provides a control valve which is safer in several respects for the personnel of the operating room, as well as for the patient under their care.

Still additionally, the present control valve allows blood to be vented therefrom in the event that reverse flow positive pressure reaches a venting pressure level, but only along a controlled and predictable path, and with a reduced flow velocity which prevents splashing and blood misting into the air.

Additional objects and advantages of the present invention will be apparent from a reading of the following detailed description of two exemplary preferred embodiments of the invention, taken in conjunction with the following drawing Figures, in which:

DESCRIPTION OF THE DRAWING FIGURES

FIG. 1 presents a schematic representation of the inventive multi-function control valve in its typical use environment of an operating room and an open-heart surgery;

FIGS. 2A and 2B, present respective external and cross sectional view of a multi-function control valve embodying the present invention;

FIGS. 3 and 4 present cross sectional views of the multi-function control valve similar to FIG. 1B, but showing component parts of the control valve in alternative operative positions;

FIG. 5 presents a cross sectional view similar to FIG. 1B, but showing an alternative embodiment of the invention; and FIG. 6 provides an isolated view of a component part of the embodiment of the invention depicted in FIGS. 1-4.

DESCRIPTION OF THE EXEMPLARY PREFERRED EMBODIMENTS

Viewing FIG. 1, a multi-function control valve 10 is schematically shown in a use environment, such as an operating room. In the operating room, a patient is undergoing open heart surgery, and the patient's heart 12 has inserted into the left ventricle 14 thereof a suction tube 16 having an open distal end 18. From the operating table, the suction tube 16 leads downwardly to a roller type of positive displacement aspiration pump 20, and to a cardiotomy reservoir 22. As is well understood, the blood and other patient fluids collected in the cardiotomy reservoir 22 is generally filtered and is otherwise treated before being reintroduced into the patient's circulatory system during or at the conclusion of the surgical procedure.

FIGS. 2 show the control valve 10 at a much enlarged scale, and in cross section in FIG. 2B. Viewing these figures, it is seen that the control valve 10 includes an elongate cylindrical two-part housing, generally referenced with the numeral 24. The housing 24 includes an inlet part 26, and an axially disposed outlet part 28. The inlet part 26 defines a pair of axially extending barbed lugs 30, which are removably captured in a respective pair of axially apertured bosses 32 defined by the outlet part 28. Additionally, the inlet housing part 26 defines a pair of axially and circumferentially extending wall portions 34 extending over and spaced radially outwardly of an underlying wall portion 36 of the outlet housing part 28 and parallel with the lugs 30. Cooperatively, the wall portions 34 and underlying wall portion 36 of the outlet housing part 28 define a radially and axially extending gap 38 opening axially toward the remainder of the outlet part 28. Consequently, as is well illustrated in FIG. 2A, the control valve 10 outwardly presents a sleek cylindrical exterior shape which is only slightly stepped and is substantially without external projections which might catch on other surrounding items. This sleekness of the control valve is especially evident when suction tubing 16 is joined to the housing 12, as can be easily visualized from the dashed lines on FIG. 2A. Also, the housing 24 is simply snapped together during manufacture of the control valve 10 by inserting the lugs 30 into the bosser 32 and moving the housing portions 26, 28 axially together.

Viewing FIG. 2B, it is seen that the housing 12 includes opposite inlet and outlet ends, 40, 42, at which respective inlet and outlet openings 44, 46 are defined. Extending between and communicating the openings 44, and 46, is a flow path, generally referenced with the numeral 48. The flow path 48 is cooperatively defined by respective aligned bores 50, and 52 of the inlet and outlet parts 26, and 28. Outwardly, the inlet part and outlet part 26, 28, each define a respective hose barb feature, referenced with the numerals 54, and 56.

Sealingly captured between a shoulder 58 on the inlet part 26, and an end surface 60 of the outlet part 28, is a radially outwardly extending flange portion 62 of a multi-function yieldably shape-retaining elastomeric valving member, generally referenced with the numeral 64 (viewing also FIG. 6). This valving member 64 includes an axially extending cylindrical portion 66, which extends axially from the flange portion into the bore 52 of the outlet part 28, and which is radially spaced inwardly thereof. Spaced from the flange 62, the valving member 64 defines a radially outwardly extending circumferentially continuous rib 68 which sealingly engages the wall portion 36 of the outlet housing part 28. Consequently, the valving member 64 cooperates with the housing 12 to define an annular chamber 70. Wall portion 36 of outlet housing part 28 defines at least a single radially extending vent port 72 opening outwardly from the chamber 70 into the gap space 38.

Downstream of the rib 68 with respect to blood flow through the valve 10 (that is, rightwardly viewing FIG. 2B), the valving member 64 includes a duck bill type of check valve feature, generally referenced with the numeral 74. This duck bill check valve feature includes a pair of juxtaposed yieldable lips 76 which sealingly cooperate with one another at a sealing line 78.

Having observed the structure of the multi-function control valve 10, attention may now be directed to its operation. As is easily understood, when the positive displacement pump 20 is operated, a negative pressure is communicated to the outlet opening 46. This negative pressure opens the duck bill lips at 78 and communicates via the inlet opening 44 and suction tubing 16 to the patient's left ventricle to aspirate blood and other fluids therefrom. This flow of aspirated fluid is represented on FIG. 2B with arrows 80.

It will be noted that inwardly, the cylindrical portion 66 defines an area 82 which is exposed to the negative pressure within flow path 48. Outwardly, the cylindrical portion 66 defines an area 84 within chamber 70 which is exposed to ambient pressure via the vent port 72. Thus, the cylindrical portion 66 defines a pair of opposed pressure-responsive areas, one of which is exposed to pressure within flow path 48, and the other of which is exposed to ambient pressure. Thus, as is illustrated in FIG. 3, in the event the negative pressure within flow path 48 reaches a certain level, the cylindrical portion 66 of the valving member 64 collapses to unseal rib 68 from wall portion 36. Consequently, ambient air is admitted to the flow path 48, as is depicted by arrows 86, to limit the level of suction which can be communicated to the patient. That is, the collapse of the cylindrical portion 66, and the unsealing of the rib 68 from wall 36 serves as a negative pressure relief valve.

On the other hand, in the event that an event of incorrect plumbing connection, reverse operation of the pump 20, or stopping of the pump 20 while the cardiotomy 22 is pressurized, or any other cause results in a reverse positive pressure being communicated to the outlet opening 46, as is indicated by the arrow 88, the duck bill lips 76 sealingly cooperate with one another at sealing line 78 to prevent this pressure from communicating to the patient's heart. Consequently, the interior of the duck bill valving member is maintained at a comparatively low pressure. However, if the reverse positive pressure were to reach a sufficiently high level, the elastomeric duck bill valving member 64 could not contain the pressure. Consequently, when this duck bill member starts to collapse inwardly on itself toward the inlet 44, the rib 68 is again unsealed from the wall portion 36, and the reverse positive pressure is vented outwardly via the vent port 72, as is indicated in FIG. 4 with arrow 90.

It will be noted that in the event that reverse flow positive pressure reaches the venting level, as described above, the vented blood is received into the gap 38 and against the outer wall portion 34. The gap 38 has a considerably larger cross sectional flow area than does the port 72 so that the flow velocity of the vented blood is greatly reduced. Also, the gap 38 directs the vented blood at a relatively low velocity along the housing portion 36 and tubing 52 axially. This housing portion and tubing provide a flow surface along which the blood will flow without spraying or misting into the operating room environment. Thus, safety for the personnel of the operating room is considerably increased by the present invention on those rare occasions when a reverse positive pressure on the control valve 10 does cause blood venting in order to protect the patient and prevent an uncontrolled venting of such a pressure.

On the other hand, and very importantly, if a positive pressure is communicated with the inlet opening 44, as can happen if the pump 20 is stopped with the suction tube 16 full of liquid which creates a liquid column pressure at the valve 10 (that is, an inlet positive pressure on the valve), then the duck bill valve member 64 communicates this pressure to the outlet opening 46 past the duck bill lips 76. However, in this case the duck bill member 64 is exposed to a positive pressure at area 82, while the surrounding area 84 is exposed to ambient. Thus, the internal positive pressure assists in maintaining the rib 68 in sealing relation with the wall portion 36, and no blood is vented from the control valve 10.

That is, the present control valve 10 performs an inlet positive pressure containment function which is totally lacking from the conventional control valves heretofore available for use in situations of open heart and other surgical procedures. Only under conditions of outlet positive pressure relieving, which is an essential safety function for the multi-function valve 10, will any blood be vented from the present inventive control valve. When such a situation of outlet positive pressure relieving does occur, as explained above, the present valve provides the additional advantage that the vent port 72 opens toward the wall portion 34 into the relatively larger annular gap 38 so that the velocity of the venting blood is reduced and a blood spray is avoided. Also, the gap 38 itself opens axially along the line of the suction tubing 16 downstream of the control valve 10 so that the venting fluid is directed to flow along the exterior surface of the valve 10 at a low velocity, and will simply flow onto the operating room floor without spitting or spraying about.

FIG. 5 depicts an alternative embodiment of the inventive control valve. In order to obtain reference numerals for use in describing the embodiment of FIG. 5, features of this embodiment which are analogous in structure or function to features described above with reference to FIGS. 1–4, are referenced on FIG. 5 with the same numeral used earlier, and having a prime added thereto. Viewing FIG. 5, it is seen that the duck bill valving member 64' includes a cylindrical portion 66' extending into the outlet part 28' of the control valve 10'. This cylindrical portion 66' is outwardly smooth, but the housing wall portion 36' defines a radially inwardly and circumferentially continuous rib 68', which sealingly cooperates with the valving member 64' to define a chamber 70'. In other structural respects, and in all functional respects, the embodiment of FIG. 5 is the same as that described above.

While the present invention has been depicted, described, and is defined by reference to particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

We claim:

1. A multi-function control valve comprising:

a housing defining an inlet, an outlet, and a flow path extending between said inlet and said outlet to communicate a flow of fluid therebetween;

a multi-function valve member sealingly disposed in said flow path and including a check valve feature preventing fluid flow from said outlet to said inlet;

said housing defining a vent port opening outwardly from said flow path downstream of the check valve feature;

said multi-function valve member including a pressure-responsive yieldable member sealingly cooperating with the housing to prevent fluid flow through said vent passage, said yieldable member comprising a cylindrical section of elastomeric material extending along said flow path, said cylindrical section comprising an inner surface and an outer surface, said yieldable member further comprising a first pressure-responsive area on said outer surface of said cylindrical section communicating with ambient, and a second pressure-responsive area on said inner surface of said cylindrical section communicating with said inlet port and isolated from said outlet port by said check valve feature, said yieldable member yielding in response to a determined pressure level on said check valve feature to open said vent port;

said pressure-responsive yieldable member on the one hand yielding in response to a certain level of negative pressure in said flow path to admit ambient air thereto via said vent port, and on the other hand said yieldable member yielding in response to said determined level of pressurized fluid communicating to said outlet port to vent pressurized fluid from said vent port; pressurized fluid communicating with said inlet port and being communicated with the outlet port via the check valve feature also acting on said second pressure-responsive area to maintain said yieldable member in sealing relation with said housing, whereby pressurized fluid communicating to said inlet port is not vented; and wherein said cylindrical section of elastomeric material defines a radially outwardly extending circumferential rib which sealingly cooperates with said housing.

2. The control valve of claim 1 wherein said cylindrical section of elastomeric material at an upstream end thereof is sealingly carried by said housing, and at a downstream end thereof said cylindrical section of elastomeric material carries said check valve feature.

3. The control valve of claim 2 wherein said check valve feature includes a pair of yieldable duck-bill lips sealingly cooperating with one another to prevent fluid flow from said outlet to said inlet and yielding to allow fluid flow in the opposite direction.

4. The control valve of claim 3 wherein said pair of duck-bill lips are integrally formed with said cylindrical section of elastomeric material.

5. The control valve of claim 1 wherein said housing includes an inlet portion and an outlet portion each respectively defining said inlet port and said outlet port and respective parts of said flow path, said inlet portion and said outlet portion defining respective confronting end surfaces, and said cylindrical section of elastomeric material defining a radially outwardly extending flange portion which is sealingly interposed between said confronting end surfaces of said housing portions.

6. The control valve of claim 5 wherein one of said housing portions includes a perforate boss, and the other of said housing portions includes a barb captively received into said perforate boss to secure said housing portions together with said flange portion sealingly interposed therebetween.

7. The control valve of claim 1 wherein said housing defines a wall portion outwardly of said vent port and in alignment therewith, said wall portion cooperating with the remainder of said housing to define a venting flow path of area significantly greater than said vent port.

8. The control valve of claim 7 wherein said housing is elongate, and said venting flow path is disposed axially of said housing length.

9. The control valve of claim 5 wherein said cylindrical section of elastomeric material defines said first pressure-responsive area between said flange thereof and said sealing cooperation of said cylindrical section of elastomeric material with said housing to isolate said vent port from said flow path.

10. The control valve of claim 9 wherein said cylindrical section of elastomeric material defines said second pressure-responsive area on about the opposite side of said cylindrical section of elastic material which defines said first pressure-responsive area.

11. A method of controlling an aspirating suction level communicating to a patient from an aspirator during a surgical procedure, said method comprising the steps of:
providing a yieldable pressure-responsive valve member comprising an elongate cylindrical section of elastomeric material having an outer surface and an inner surface, said cylindrical section of elastomeric material defining a first area on said outer surface thereof communicating with ambient and an opposite second area on said inner surface thereof communicating with said aspirating suction;
causing said yieldable pressure-responsive valve member to communicate ambient air to said aspirator at a certain level of aspiration suction;
providing a check valve isolating both said patient and said second pressure-responsive area from reverse flow positive pressure and defining a third pressure-responsive area effective to yield said valve member at a determined level of reverse flow positive pressure to communicate said reverse flow positive pressure to ambient; and
communicating an inlet positive pressure to said second pressure-responsive area to assist said pressure-responsive valve member in sealingly engaging said housing to prevent venting of said inlet positive pressure.

12. The method of claim 11 further including the steps of configuring said housing to define a through passageway, and using a singular unitary valving member to define all of said first, second, and third pressure-responsive areas as well as said check valve.

13. The method of claim 12 wherein said configuring step includes the step of forming said unitary valving member to also define a pair of sealingly cooperating duck-bill check valve lips forming said check valve and defining said third pressure-responsive area.

14. A multi-function control valve comprising:
a housing defining an inlet, an outlet, and a flow path extending between said inlet and said outlet to communicate a flow of fluid therebetween;
a multi-function valve member sealingly disposed in said flow path and including a check valve feature preventing fluid flow from said outlet to said inlet;
said housing defining a vent port opening outwardly from said flow path downstream of the check valve feature;
said multi-function valve member including a pressure-responsive yieldable member sealingly cooperating with the housing to prevent fluid flow through said vent passage, said yieldable member comprising a cylindrical section of elastomeric material extending along said flow path, said cylindrical section comprising an inner surface and an outer surface, said yieldable member further comprising a first pressure-responsive area on said outer surface of said cylindrical section communicating with ambient, and a second pressure-responsive area on said inner surface of said cylindrical section communicating with said inlet port and isolated from said outlet port by said check valve feature, said yieldable member yielding in response to a determined pressure level on said check valve feature to open said vent port;
said pressure-responsive yieldable member on the one hand yielding in response to a certain level of negative pressure in said flow path to admit ambient air thereto via said vent port, and on the other hand said yieldable member yielding in response to said determined level of pressurized fluid communicating to said outlet port to vent pressurized fluid from said vent port; pressurized fluid communicating with said inlet port and being communicated with the outlet port via the check valve feature also acting on said second pressure-responsive area to maintain said yieldable member in sealing relation with said housing, whereby pressurized fluid communicating to said inlet port is not vented; and
wherein said housing defines a radially inwardly extending circumferential rib which sealingly cooperates with said cylindrical section of elastomeric material.

15. The control valve of claim 14 wherein said cylindrical section of elastomeric material at an upstream end thereof is sealingly carried by said housing, and at a downstream end thereof said cylindrical section of elastomeric material carries said check valve feature.

16. The control valve of claim 15 wherein said check valve feature includes a pair of yieldable duck-bill lips sealingly cooperating with one another to prevent fluid flow from said outlet to said inlet and yielding to allow fluid flow in the opposite direction.

17. The control valve of claim 16 wherein said pair of duck-bill lips are integrally formed with said cylindrical section of elastomeric material.

18. The control valve of claim 14 wherein said housing includes an inlet portion and an outlet portion each respectively defining said inlet port and said outlet port and respective parts of said flow path, said inlet portion and said outlet portion defining respective confronting end surfaces, and said cylindrical section of elastomeric material defining a radially outwardly extending flange portion which is sealingly interposed between said confronting end surfaces of said housing portions.

19. The control valve of claim 18 wherein one of said housing portions includes a perforate boss, and the other of said housing portions includes a barb captively received into said perforate boss to secure said housing portions together with said flange portion sealingly interposed therebetween.

20. The control valve of claim 14 wherein said housing defines a wall portion outwardly of said vent port and in alignment therewith, said wall portion cooperating with the remainder of said housing to define a venting flow path of area significantly greater than said vent port.

21. The control valve of claim 20 wherein said housing is elongate, and said venting flow path is disposed axially of said housing length.

22. The control valve of claim 20 wherein said cylindrical section of elastomeric material defines said first pressure-responsive area between said flange thereof and said sealing cooperation of said cylindrical section of elastomeric material with said housing to isolate said vent port from said flow path.

23. The control valve of claim 22 wherein said cylindrical section of elastomeric material defines said second pressure-responsive area on about the opposite side of said cylindrical section of elastic material which defines said first pressure-responsive area.

* * * * *